US008808711B2

(12) United States Patent
Oster et al.

(10) Patent No.: US 8,808,711 B2
(45) Date of Patent: Aug. 19, 2014

(54) MENINGOCOCCAL OUTER MEMBRANE VESICLES

(75) Inventors: Philipp Oster, Siena (IT); Mariagrazia Pizza, Siena (IT); Rino Rappouli, Siena (IT)

(73) Assignee: Novartis AG, Basel (CH)

( * ) Notice: Subject to any disclaimer, the term of this patent is extended or adjusted under 35 U.S.C. 154(b) by 723 days.

(21) Appl. No.: 11/661,996

(22) PCT Filed: Sep. 5, 2005

(86) PCT No.: PCT/IB2005/002801
§ 371 (c)(1),
(2), (4) Date: Oct. 19, 2007

(87) PCT Pub. No.: WO2006/024946
PCT Pub. Date: Mar. 9, 2006

(65) Prior Publication Data
US 2008/0063665 A1    Mar. 13, 2008

(30) Foreign Application Priority Data
Sep. 3, 2004   (GB) .................................. 0419627.5

(51) Int. Cl.
*A61K 39/095*     (2006.01)
(52) U.S. Cl.
USPC ....................................................... 424/249.1
(58) Field of Classification Search
None
See application file for complete search history.

(56) References Cited

U.S. PATENT DOCUMENTS

| | | | |
|---|---|---|---|
| 6,180,111 B1 | 1/2001 | Stein et al. | |
| 6,355,253 B1 | 3/2002 | Zlotnick | |
| 6,451,317 B1 | 9/2002 | Milan et al. | |
| 6,936,261 B2 | 8/2005 | Granoff et al. | |
| 7,018,636 B1 | 3/2006 | Bhattacharjee et al. | |
| 7,384,645 B2 | 6/2008 | Foster et al. | |
| 2006/0029621 A1 | 2/2006 | Granoff et al. | |
| 2006/0240045 A1 | 10/2006 | Berthet et al. | |
| 2009/0123499 A1 * | 5/2009 | Devos et al. ............... | 424/250.1 |

FOREIGN PATENT DOCUMENTS

| | | |
|---|---|---|
| EP | 0011243 | 4/1982 |
| EP | 1741443 | 10/2007 |
| WO | WO-99/61053 | 12/1999 |
| WO | WO 0109350 A2 * | 2/2001 |
| WO | WO-01/34642 | 5/2001 |
| WO | WO-01/91788 | 12/2001 |
| WO | WO 02/09643 | 2/2002 |
| WO | WO 03009869 A1 * | 2/2003 |
| WO | WO 03/105890 | 12/2003 |
| WO | WO 2004/014418 | 2/2004 |
| WO | WO 2004/019977 | 3/2004 |
| WO | WO 2004/048404 | 6/2004 |
| WO | WO 2004/054611 | 7/2004 |
| WO | WO-2005/004908 | 1/2005 |
| WO | WO-2005/064021 | 7/2005 |

OTHER PUBLICATIONS

Norheim, G. et al. "Immunogenicity and bactericidal activity in mice of an outer membrane protein vesicle vaccine against Neisseria . . . " Vaccine, 22: 2171-2180 (2004).
Peeters, C. et al. "Phase I clinical trial with a hexavalent PorA containing meningococcal outer membrane vesicle vaccine," Vaccine, 14(10): 1009-1015 (1996).
De Kleijn, E.D. et al. "Immunogenicity and safety of a hexavalent meningococcal outer-membrane-vesicle vaccine in children of 2-3 and 7-8 years of age," Vaccine, 18:1456-1466 (2000).
Arigita, C. at al. "Stability of mono- and trivalent meningococcal outer membrane vesicle vaccines," Vaccine, vol. 22, No. 5-0, 2004, pp. 630-643.
Bjune et al., "Effect of outer membrane vesicle vaccine against group B meningococcal disease in Norway," Lancet 338(8775):1093-1096, 1991.
Boslego J, et al. (1995). Efficacy, safety, and immunogenicity of a meningococcal group B (15:P1.3) outer membrane protein vaccine in Iquique, Chile. Chilean National Committee for Meningococcal Disease. Vaccine 13:821-829.
Corbel, "Control testing of combined vaccines: a consideration of potential problems and approaches," *Biologicals* 22(4):353-360, 1994.
Dalseg et al. (May 14, 1999). "Outer membrane vesicles from group B meningococci are strongly immunogenic when given intranasally to mice" Vaccine 17(19):2336-2345.
de Moraes JC, et al. (1992). Protective efficacy of a serogroup B meningococcal vaccine in Sao Paulo, Brazil. Lancet 340: 1074-1078.
Debbag et al., "Evaluation of Adverse Reactions Associated to Antimeningococcal BC Vaccination in 16,700 Children" Clinical Infectious Diseases, vol. 21, pp. 790-A420 (Sep. 1995).
Fredrikson et al. (1991). Production, characterization and control of MenB-vaccine "Folkehelsa": an outer membrane vesicle vaccine against group B meningococcal disease. NIPH Annals 14:67-79.
Fukasawa et al. "Adjuvant can improve protection induced by OMV vaccine against *Neisseria meningitidis* serogroups B/C in neonatal mice" FEMS Immunal. Med. Microbiol. 41:205-210, Jul. 1, 2004.

(Continued)

*Primary Examiner* — Brian J Gangle
(74) *Attorney, Agent, or Firm* — Morrison & Foerster LLP

(57) ABSTRACT

OMVs targeted against specific epidemic strains can be highly effective in controlling localized outbreaks of disease. In combination with large-scale and reproducible manufacturing techniques, a vaccine can be rapidly produced after an outbreak. The invention provides a method for preparing a meningococcal outer membrane vesicle (OMV) vaccine, comprising the steps of: (i) identifying the serosubtype of a meningococcal strain associated with an outbreak of meningococcal meningitis; (ii) preparing OMVs from a meningococcal strain having the serosubtype identified in step (i) for use in vaccine manufacture. The method may comprise one or both of the further steps of (iii) formulating said OMVs as a vaccine; and (iv) distributing said vaccine in a geographical area affected by or likely to be affected by said outbreak. The meningococcal strain will typically be in serogroup B, but may be instead by in serogroup A, C, W135, Y, etc.

12 Claims, No Drawings

(56) References Cited

OTHER PUBLICATIONS

Fukasawa et al. (1999) "*Neisseria meningitidis* serogroup C polysaccharide and serogroup B outer membrane vesicle conjugate as a bivalent meningococcus vaccine candidate." Vaccine 17:2951-2958.

Gao et al. (1996). "Study on the LOS Antigenicity of 2 Candidate Strains for Meningococcal Vaccine of Serogroup B," Zhonghua Weishengwuxue He Mianyixue Zazhi 16(6):405-408. (English language Abstract only).

Henry, T. at al. "Improved methods for producing outter membrane vesicles in Gram-negative bacteria," Research in Microbiology, 2004, 155:437-446.

Hoiby et al., "The Norwegian meningococcal serogroup B outer membrane vesicle vaccine protection trials: case tracing, meningococcal antigen detection and serological diagnosis," NIPH Annals 14(2):107-123, 1991.

Hoist et al. (2003). "Serum bactericidal activity correlates with the vaccine efficacy of outer membrane vesicle vaccines against *Neisseria meningitidis* serogroup B disease," Vaccine 21(7-8):734-737.

International Preliminary Examination Report mailed Aug. 23, 2000, for international patent application No. PCT/US99/11977, filed May 28, 1999, 7 pages.

Katial et al. (2002). "Immunogenicity and Safety Testing of a Group B Intranasal Meningococcal Native Outer Membrane Vesicle Vaccine," Infection and Immunity 70(2):702-707.

Koeberling et al. (2007). "Improved immunogenicity of a H44/76 group B outer membrane vesicle vaccine with over-expressed genome-derived Neisserial antigen 1870," Vaccine 25(10):1912-1920.

Milagres L G et al. (Aug. 2000) "Bactericidal antibody response to Neisseria meningitidis serogroup B in patients with bacterial meningitis: effect of immunization with an outer membrane protein vaccine," FEMS Immunology and Medical Microbiology 28(4):319-327.

Norheim et al. (2005) "Development and characterisation of outer membrane vesicle vaccines against serogroup A *Neisseria meningitidis*" Vaccine 23(29):3762-3774.

O'Hallahan J, et al. 2004. The strategy to control New Zealand's epidemic of Group B meningococcal disease. PIDJ 23: S293-S298.

Oster P, O'Hallahan J, Aaberge I, Tilman S, Ypma E, Martin D. 2007. Immunogenicity and safety of a strain-specific MenB OMV vaccine delivered to under 5-year olds in New Zealand. Vaccine. 25:3075-9.

Parkhill, J. et al. (Mar. 2000). "Complete DNA Sequence of a Serogroup a Strain of *Neisseria meningitides* Z2491," Nature 404(6777):502-506.

Perkins et al. (1998). "Immunogenicity of two efficacious outer membrane protein-based serogroup B meningococcal vaccines among young adults in Iceland," *The Journal of Infectious Disease* 177:683-691.

Rosenqvist et al. (1995). "Human Antibody Response to Meningococcal Outer Membrane Antigens after Three Doses of the Norwegian Group B Meningococcal Vaccine," Infection and Immunity 63(12):4642-4652.

Rosenqvist et al., "Effect of Aluminum Hydroxide and Meningococcal Serogroup C Capsular Polysaccharide on the Immunogenecity and Reactogenecity of a Group B *Neisseria meningitidis* Outer Membrane Vesicle Vaccine", Developments in Biological Standardization, vol. 92, pp. 323-333, (1998).

Sierra GV, et al. (1991). Vaccine against group B *Neisseria meningitidis*: protection trial and mass vaccination results in Cuba. NIPH Ann 14: 195-207.

Van der Ley et al. (1992). "Construction of a Multivalent Meningococcal Vaccine Strain Based on the Class I Outer Membrane Protein," *Infection and Immunity* 60(8): 3516-3161.

Van der Ley & Steeghs (2003) "Lessons from an LPS-deficient *Neisseria meningitidis* mutant" Journal of Endotoxin Research 9(2):124-128.

Verheul et al., (1991). "Preparation, Characterization, and Immunogenicity of Meningococcal Immunotype L2 and L3,7,9 Phosphoethanolamine Group-Containing Oligosaccharide-Protein Conjugates," Infection and Immunity 59(3):843-851.

Wedege et al. (2003). "Antibody specificities and effect of meningococcal carriage in icelandic teenagers receiving the Norwegian serogroup B outer membrane vesicle vaccine," Infect. Immun. 71:3775-3781.

Williams et al., (2007) "Proteomic analysis of outer membranes and vesicles from wild-type serogroup B Neisseria meningitidis and a lipopolysaccharide-deficient mutant" Infection and Immunity 75(3):1364-1372.

\* cited by examiner

MENINGOCOCCAL OUTER MEMBRANE VESICLES

RELATED APPLICATIONS

This application is the U.S. National Phase of International Application No. PCT/IB32005/002801, filed Sep. 5, 2005 and published in English, which claims priority to Great Britain Application No. 0419627.5, filed Sep. 3, 2004. The teachings of the above applications are incorporated in their entirety by reference.

All documents cited herein are incorporated by reference in their entirety.

TECHNICAL FIELD

This invention is in the field of meningococcal outer membrane vesicles for immunisation purposes.

BACKGROUND ART

One of the various approaches to immunising against infection by *Neisseria meningitidis* (meningococcus) is to use outer membrane vesicles (OMVs). An efficacious OMV vaccine against serogroup B has been produced by the Norwegian National Institute of Public Health ['MenBvac™'; e.g. ref. 1] but, although this vaccine is safe and prevents MenB disease, efficacy is limited to the homologous serotype used to make the vaccine.

The 'RIVM' vaccine is based on OMVs containing six different PorA subtypes. It has been shown to be immunogenic in children in phase II clinical trials [2].

Reference 3 discloses a vaccine against different pathogenic serotypes of serogroup B meningococcus based on OMVs which retain a protein complex of 65-kDa. Reference 4 discloses a vaccine comprising OMVs from genetically-engineered meningococcal strains, with the OMVs comprising: at least one Class 1 outer-membrane protein (OMP) but not comprising a Class 2/3 OMP. Reference 5 discloses OMVs comprising OMPs which have mutations in their surface loops and OMVs comprising derivatives of meningococcal lipopolysaccharide (LPS). Reference 6 discloses a process for preparing OMV-based vaccines for serogroup A meningococcus.

There have been various proposals to improve OMV efficacy. Reference 7 discloses compositions comprising OMVs supplemented with transferrin binding proteins (e.g. ThpA and TbpB) and/or Cu,Zn-superoxide dismutase. Reference 8 discloses compositions comprising OMVs supplemented by various proteins. Reference 9 discloses preparations of membrane vesicles obtained from *N. meningitidis* with a modified fur gene. Reference 26 teaches that nspA expression should be up-regulated with concomitant porA and cps knockout. Further knockout mutants of *N. meningitidis* for OMV production are disclosed in references 26 to 28. In contrast to these attempts to improve OMVs by changing expression patterns, reference 29 focuses on changing the methods for OMV preparation, and teaches that antigens such as NspA can be retained during vesicle extraction by avoiding the use of detergents such as deoxycholate.

The failure of meningococcal OMVs to elicit cross-protection against non-homologous serotypes limits their use as general vaccines, but they can be very useful in epidemic situations where disease is characterised by pathogenic strains that are essentially clonal. Thus the Finlay Institute vaccine (VA-MENGOC-BC™) has been useful in Latin America, where serogroup B disease had been dominated by the P1.19,15 serotype, but has not been effective elsewhere [10]. Similarly, the Chiron MeNZB™ vaccine has been targeted at the epidemic strain (P1.7b,4, known as P1.7-2,4 by recent nomenclature) that has been prevalent in New Zealand since 1991.

Reference 11 discloses vaccine comprising multivalent meningococcal bleb compositions, comprising a first bleb derived from a meningococcal strain with a serosubtype prevalent in a country of use, and a second bleb derived from a strain that need not have a serosubtype prevent in a country of use.

It is an object of the invention to provide further and improved meningococcal OMV preparations.

DISCLOSURE OF THE INVENTION

Experience with MeNZB™ has shown that OMVs targeted against specific epidemic strains can be highly effective in controlling localised outbreaks of disease. In combination with large-scale and reproducible manufacturing techniques, a vaccine can be rapidly produced after an outbreak. Thus the invention provides a method for preparing a meningococcal outer membrane vesicle (OMV) vaccine, comprising the steps of: (i) identifying the serosubtype of a meningococcal strain associated with an outbreak of meningococcal meningitis; (ii) preparing OMVs from a meningococcal strain having the serosubtype identified in step (i) for use in vaccine manufacture. The method may comprise one or both of the further steps of: (iii) formulating said OMVs as a vaccine; and (iv) distributing said vaccine in a geographical area affected by or likely to be affected by said outbreak. The invention also provides the same method, but omitting step (i), for situations where the relevant serosubtype has already been identified. The meningococcal strain will typically be in serogroup B, but may be instead by in serogroup A, C, W135, Y, etc.

Experience with MeNZB™ has also suggested to the inventors that OMVs will be useful for immunising against meningococcal serogroups A, C, W135 and Y, either alone or in combination, and that these might be cheaper to manufacture than the currently-proposed conjugate vaccines. Thus the invention provides: (a) a composition comprising outer membrane vesicles from a serogroup C strain of meningococcus; (b) a composition comprising outer membrane vesicles from a serogroup W135 strain of meningococcus; (c) a composition comprising outer membrane vesicles from a serogroup Y strain of meningococcus; and (d) a composition comprising outer membrane vesicles from two or more of serogroups A, B, C, W135 and Y of meningococcus. Within (d), preferred compositions include the following serogroup mixtures: A+B; A+C; A+W135; A+Y; B+C; B+W135; B+Y; C+W135; C+Y; W135+Y; A+B+C; A+B+W135; A+B+Y; A+C+W135; A+C+Y; A+W135+Y; B+C+W135; B+C+Y; C+W135+Y; A+B+C+W135; A+B+C+Y; B+C+W135+Y; and A+B+C+W135+Y.

Because sub-capsular antigens are shared between serogroups then OMVs (and OMV mixtures) can protect against more than just the serogroup from which they are prepared. For example, the sub-capsular antigens from serogroup A and W135 strains seen in sub-saharan Africa are shred with serogroup C and Y strains seen elsewhere in the world. Thus the invention provides the use of OMVs from a meningococcal strain in a first serogroup for protecting against one or more meningococcal strains in a second serogroup, wherein said first and second serogroups are different. The strains preferably share sub-capsular antigens, and may have the same subtype, serosubtype and/or immunotype, even though they have different serogroups. A mixture of OMVs from serogroups A and W135 is preferred, as is a mixture of OMVs from serogroups C and Y.

Experience with MeNZB™ has also suggested to the inventors that a mixture of OMVs from the strains used for the New Zealand OMVs, the Norway OMVs and the Cuban OMVs would be usefully efficacious. Thus the invention provides a composition comprising outer membrane vesicles from two or three of: (i) a serosubtype P1.7b,4 meningococcus; (ii) a serosubtype P1.7,16 meningococcus; and (iii) a serosubtype P1.9,15 meningococcus. The different OMVs are preferably in admixture but, alternatively, they may be in separate containers within a kit.

In combining OMVs from different serosubtypes, the inventors have found that doses for individual serosubtypes can be reduced without loss of efficacy. Whereas VA-MENGOC-B™ contains 50 µg of OMVs (0.5 ml, volume), HexaMen™ includes around 1 mg OMVs (0.3 ml volume), and both MenBVac™ and MeNZB™ contain 25 µg OMVs (0.5 ml volume), measured as total protein, the inventors have found that the dose of individual OMVs can be reduced when a mixture is used without loss of individual efficacy. Thus the invention provides a composition comprising outer membrane vesicles from a first meningococcal serosubtype and a second meningococcal serosubtype, wherein the concentration of OMVs from the first serosubtype is less than 45 µg/ml and the concentration of OMVs from the second serosubtype is less than 45 µg/ml. The invention also provides a composition comprising outer membrane vesicles from at least two meningococcal serosubtypes, wherein the combined concentration of OMVs is less than 90 µg/ml. The invention also provides a composition comprising outer membrane vesicles from n different meningococcal serosubtypes, wherein the concentration of OMVs from each of the n serosubtypes is less than 45 µg/ml (i.e. a total OMV dose of less than 45n µg/ml). The value of n may be 1, 2, 3, 4, 5, 6, etc.

The invention also provides a kit comprising OMVs prepared from n different serosubtypes. The vesicles can be kept and stored separately in the kit until they are required to be used together e.g. as an admixture, or for simultaneous separate or sequential use. Similarly, the invention provides a process comprising: preparing n sets of OMVs, one from each of n different serosubtypes; and combining the n sets of vesicles. The different sets can be combined into a kit or into an admixture.

The invention also provides a composition comprising OMVs prepared from a serogroup B meningococcal strain having a P1.7b,4 serosubtype, wherein the concentration of OMVs in the composition is about 50 µg/ml. The composition preferably includes an aluminium hydroxide adjuvant and a histidine buffer. The composition may be given in a dose volume of about 0.5 ml.

The Vesicles

The invention is based on outer membrane vesicles (OMVs) prepared from *Neisseria meningitidis*. The term "OMV" includes any proteoliposomic vesicle obtained by disrupting a bacterial outer membrane to form vesicles of the outer membrane that include protein components of the outer membrane. OMVs are prepared artificially from bacteria (e.g. by detergent treatment, or by non-detergent means [29]). The term also encompasses blebs, microvesicles (MVs [12]) and 'native OMVs' ('NOMVs' [13]), which are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 14 & 15 describe *Neisseria* with high MV production.

OMVs can be prepared in various ways. Methods for obtaining suitable preparations are disclosed in, for instance, the references cited herein. Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [16 & 17] being preferred for treating *Neisseria*) at a pH sufficiently high not to precipitate the detergent [6]. Other techniques may be performed substantially in the absence of detergent [29] using techniques such as sonication, homogenisation, microfluidisation, cavitation, osmotic shock, grinding, French press, blending, etc.

A preferred method for OMV preparation involves ultrafiltration [18] instead of high speed centrifugation on crude OMVs. This allows much larger amounts of OMV-containing supernatant to be processed in a much shorter time (typically >15 liters in 4 hours, compared to <1.5 liters in 10 hours), and avoids the need to redisperse OMVs after centrifugation. Ultracentrifugation allows large quantities of OMVs to be prepared much more easily, and permits the rapid production of OMVs from a strain of choice, for use in vaccine preparation.

Meningococcal Strains Used for Vaccine Preparation

Identifying the serosubtype of a meningococcal strain of interest can be achieved using standard techniques, based on the class I porin outer membrane protein (PorA). Once a serosubtype has been determined then it is routine to search for other known strains that share the same serosubtype. The other strains may share serogroup and/or serotype (PorB) with the first strain, but this will not necessarily be the case. In general, however, it is preferred to match both serogroup and serosubtype.

Meningococcal strains used according to the invention will generally be in one of the following serogroups: A, B, C, W135, or Y.

Meningococcal strains used according to the invention will generally not be strains that express multiple serosubtypes (i.e. multiple PorA alleles). Thus preferred bacteria for use with the invention will express a single PorA sequence i.e. they will be of a single serosubtype.

It is also possible to use strains in which PorA has been down-regulated e.g. in which the amount of PorA has been reduced by at least 20% (e.g. ≥30%, ≥40%, ≥50%, ≥60%, ≥70%, ≥80%, ≥90%, ≥95%, etc.), or even knocked out, relative to wild-type levels (e.g. relative to strain H44/76, as disclosed in reference 11).

Meningococci used according to the invention may be of any serotype (e.g. 1, 2a, 2b, 4, 14, 15, 16, etc.) and/or of any immunotype (e.g. L1; L3,3,7; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref. 19] e.g. the ET-37 complex is the ST-11 complex by MLST, the ET-5 complex is ST-32 (ET-5), lineage 3 is ST-41/44, etc.

Meningococci may have one or more knockout mutations of gene(s). To reduce pyrogenic activity, for instance, the bacterium should have low endotoxin (LPS) levels, and this can be achieved by knockout of enzymes involved in LPS biosynthesis. Suitable mutant bacteria are already known e.g. mutant *Neisseria* [20,21] and mutant *Helicobacter* [22]. Processes for preparing LPS-depleted outer membranes from Gram-negative bacteria are disclosed in reference 23.

As well as down-regulating expression of specific proteins, the bacterium may over-express (relative to the corresponding wild-type strain) immunogens such as NspA, protein 287 [8], protein 741 [30], TbpA [7], TbpB [7], superoxide dismutase [7], etc.

As well as having knockouts of particular endogenous genes, the bacterium may express one or more genes that are not endogenous. For example, the invention may use a recombinant strain that expresses new genes relative to the corresponding wild-type strain. Expression of non-endogenous genes in this way can be achieved by various techniques e.g. chromosomal insertion (as used for introducing multiple PorA genes [24]), knockin mutations, expression from extrachromosomal vectors (e.g. from plasmids), etc.

The bacterium may also include one or more of the knockout and/or over-expression mutations disclosed in references 25 to 30. Preferred genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB [25]; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, ThpA, and/or TbpB [26]; (c) ExbB, ExbD, rmpM, CtrA, CtrB, CtrD, GalE, LbpA, LpbB, Opa, Opc, PilC, PorB, SiaA, SiaB, SiaC, SiaD, ThpA, and/or TbpB [27]; and (d) CtrA, CtrB, CtrD, FrpB, OpA, OpC, PilC, PorB, SiaD, SynA, SynB, and/or SynC [28].

As well as combining OMVs based on different serosubtypes, combinations may be made according to other criteria. Example criteria include: serotype (PorB, class 2 or 3 OMP); immunotype (lipopolysaccharide or lipooligosaccharide); geographical origin of the strains; local prevalence of clinical strains; hypervirulent lineage e.g. two or more of subgroups I, III and IV-1, ET-5 complex, ET-37 complex, A4 cluster and lineage 3; multilocus sequence type (MLST) [19]; more than one of the three different NMB1870 variants [31].

OMV Dosing

Existing meningococcal OMV vaccines offer pharmaceutical, posological and formulation guidance for performing the invention. For example, VA-MENGOC-BC™ is an injectable suspension in 0.5 ml that contains 50 µg OMV from strain Cu-385-83 and 50 µg serogroup C capsular polysaccharide, absorbed to 2 mg of an aluminium hydroxide gel, plus 0.01% thiomersal and phosphate buffer. MeNZB™ is also a 0.5 ml suspension, and contains 25 µg OMV from strain NZ98/254 adsorbed on 1.65 mg of an aluminium hydroxide adjuvant, with a histidine buffer and sodium chloride. MenBvac is similar to MeNZB™, but is prepared from strain 44/76.

The concentration of OMVs for each subtype will be high enough to provide protective immunity after administration to a patient. The concentration of OMVs in compositions of the invention will generally be between 10 and 500 µg/ml, preferably between 25 and 200 µg/ml, and more preferably about 50 µg/ml or about 100 µg/ml (expressed in terms of total protein in the OMVs).

Where a composition include OMVs from more than one meningococcal serosubtype, however, the inventors have found that doses for individual serosubtypes can be reduced without loss of efficacy. In particular, the dose of the New Zealand and Norwegian subtypes can be halved from 25 µg to 12.5 µg in a 0.5 ml dose without loss of immunogenicity. Thus a composition of the invention with outer membrane vesicles from more than one meningococcal subtype can include less than the 100 µg/ml that would a priori be expected based on simple mixing of MenBvac™ and MeNZB™, and less than the 150 µg/ml that would a priori be expected based on simple mixing of VA-MENGOC-BC™ with either MenBvac™ or MeNZB™. Thus such compositions of the invention will have a combined OMV concentration of no more than 90 µg/ml (e.g. no more than 80 µg/ml, 70 µg/ml, 60 µg/ml, 50 µg/ml, 40 µg/ml, 30 µg/ml, or even lower).

More generally, where a composition includes outer membrane vesicles from n different meningococcal subtypes, the concentration of OMVs from each of the subtype is less than 45 µg/ml (e.g. less than 40 µg/ml, 35 µg/ml, 30 µg/ml, 25 µg/ml, 20 µg/ml, or even lower). A concentration of about 25 µg/ml is preferred.

Where a composition includes outer membrane vesicles from n different meningococcal subtypes, the amount of OMVs for each subtype is preferably within ±10% of each other i.e. the composition includes substantially equal masses of each OMV. In some circumstances, however, the amount of one subtype may be about x times greater than the amount of another subtype, where x is 2, 3 or 4 e.g. the composition could include a double dose of one subtype relative to other subtype(s) in the composition.

Pharmaceutical Compositions Containing OMVs

Compositions of the invention may be pharmaceutical compositions that include a pharmaceutically acceptable carrier. Such compositions can be prepared using a process comprising the step of admixing OMVs with the pharmaceutically acceptable carrier.

Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, sucrose, and the like, may be present. Sterile pyrogen-free, phosphate-buffered physiologic saline is a typical carrier (e.g. based on water for injection). A thorough discussion of pharmaceutically acceptable excipients is available in reference 32.

Compositions of the invention will typically be in aqueous form (e.g. solutions or suspensions) rather than in a dried form (e.g. lyophilised). Aqueous compositions are also suitable for reconstituting other vaccines from a lyophilised form (e.g. a lyophilised Hib conjugate vaccine, a lyophilised meningococcal conjugate vaccine, etc.). Where a composition of the invention is to be used for such extemporaneous reconstitution, the invention provides a kit, which may comprise two vials, or may comprise one ready-filled syringe and one vial, with the aqueous contents of the syringe being used to reactivate the dried contents of the vial prior to injection.

Compositions of the invention may be presented in vials, or they may be presented in ready-filled syringes. The syringes may be supplied with or without needles. Compositions may be packaged in unit dose form or in multiple dose form. A syringe will generally include a single dose of the composition, whereas a vial may include a single dose or multiple doses. For multiple dose forms, therefore, vials are preferred to pre-filled syringes.

Effective dosage volumes can be routinely established, but a typical human dose of the composition has a volume of about 0.5 ml e.g. for intramuscular injection. The RIVM OMV-based vaccine was administered in a 0.5 ml volume [33] by intramuscular injection to the thigh or upper arm. MeNZB™ is administered in a 0.5 ml by intramuscular injection to the anterolateral thigh or the deltoid region of the arm. Similar doses may be used for other delivery routes e.g. an intranasal OMV-based vaccine for atomisation may have a volume of about 100 μl or about 130 μl per spray [13], with four sprays administered to give a total dose of about 0.5 ml.

The pH of the composition is preferably between 6 and 8, and more preferably between 6.5 and 7.5 (e.g. about 7). The pH of the RIVM OMV-based vaccine is 7.4 [34], and a pH<7.5 is preferred for compositions of the invention. Stable pH may be maintained by the use of a buffer e.g. a Tris buffer, a phosphate buffer, or a histidine buffer. Compositions of the invention will generally include a buffer. If a composition comprises an aluminium hydroxide salt, it is preferred to use a histidine buffer [35] e.g. at between 1-10 mM, preferably about 5 mM. The RIVM OMV-based vaccine maintains pH by using a 10 mM Tris/HCl buffer. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the amount of protein per dose. A dose of about 0.9 mg protein per ml is typical for OMV-based intranasal vaccines [13].

Meningococci affect various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 36 & 37]. Injectables for intramuscular administration are typical.

Compositions of the invention may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions of the invention may comprise detergent e.g. a Tween (polysorbate), such as Tween 80. Detergents are generally present at low levels e.g. <0.01%.

Compositions of the invention may include residual detergent (e.g. deoxycholate) from OMV preparation. The amount of residual detergent is preferably less than 0.4 μg (more preferably less than 0.2 μg) for every μg of protein.

Compositions of the invention may include LPS from meningococcus. The amount of LPS is preferably less than 0.12 μg (more preferably less than 0.05 μg) for every μg of protein.

Compositions of the invention may include sodium salts (e.g. sodium chloride) to give tonicity. A concentration of 10±2 mg/ml NaCl is typical. The concentration of sodium chloride is preferably about 9 mg/ml.

Compositions of the invention will generally be administered in conjunction with other immunoregulatory agents. In particular, compositions will usually include one or more adjuvants, and the invention provides a process for preparing a composition of the invention, comprising the step of admixing vesicles of the invention with an adjuvant e.g. in a pharmaceutically acceptable carrier. Suitable adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 38], or mixtures of different mineral compounds, with the compounds taking any suitable form (e.g. gel, crystalline, amorphous, etc.), and with adsorption being preferred. The mineral containing compositions may also be formulated as a particle of metal salt [39].

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 μg $Al^{3+}$ per dose. Where an aluminium phosphate it used and it is desired not to adsorb an antigen to the adjuvant, this is favoured by including free phosphate ions in solution (e.g. by the use of a phosphate buffer).

The RIVM vaccine was tested with adsorption to either an aluminium phosphate or an aluminium hydroxide adjuvant, and the aluminium phosphate adjuvant was found to give superior results [34]. The MeNZB™, MenBvac™ and VA-MENINGOC-BC™ products all include an aluminium hydroxide adjuvant.

A typical dose of aluminium adjuvant is about 3.3 mg/ml (expressed as $Al^{3+}$ concentration).

B. Oil Emulsions

Oil emulsion compositions suitable for use as adjuvants in the invention include squalene-water emulsions, such as MF59 [Chapter 10 of ref. 38; see also ref. 40] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of ref. 38]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 41. Saponin formulations may also comprise a sterol, such as cholesterol [42].

Combinations of saponins and cholesterols can be used to form unique particles called immunostimulating complexes (ISCOMs) [chapter 23 of ref. 38]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 42-44. Optionally, the ISCOMS may be devoid of extra detergent [45].

A review of the development of saponin based adjuvants can be found in refs. 46 & 47.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 48-53. Virosomes are discussed further in, for example, ref. 54

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 55. Such "small particles" of 3dMPL are small enough to be sterile filtered through a 0.22 μm membrane [55]. Other non-toxic LPS derivatives include monophosphoryl lipid A mimics, such as aminoalkyl glucosaminide phosphate derivatives e.g. RC-529 [56,57].

Lipid A derivatives include derivatives of lipid A from *Escherichia coli* such as OM-174. OM-174 is described for example in refs. 58 & 59.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 60, 61 and 62 disclose possible analog substitutions e.g. replacement of guanosine with 2'-deoxy-7-deazaguanosine. The adjuvant effect of CpG oligonucleotides is further discussed in refs. 63-68.

The CpG sequence may be directed to TLR9, such as the motif GTCGTT or TTCGTT [69]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 70-72. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 69 & 73-75.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or *pertussis* ("PT"). The use of detoxified ADP-ribosylating toxins as mucosal adjuvants is described in ref. 76 and as parenteral adjuvants in ref. 77. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 78-85. Numerical reference for amino acid substitutions is preferably based on the alignments of the A and B subunits of ADP-ribosylating toxins set forth in ref. 86, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [87], etc.) [88], interferons (e.g. interferon-?), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [89] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [90].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 38)

Examples of liposome formulations suitable for use as adjuvants are described in refs. 91-93.

J. Polyoxyethylene ether and polyoxyethylene ester Formulations

Adjuvants suitable for use in the invention include polyoxyethylene ethers and polyoxyethylene esters [94]. Such formulations further include polyoxyethylene sorbitan ester surfactants in combination with an octoxynol [95] as well as polyoxyethylene alkyl ethers or ester surfactants in combination with at least one additional non-ionic surfactant such as an octoxynol [96]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 97 and 98.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e,g. "Resiquimod 3M"), described further in refs. 99 and 100.

The invention may also comprise combinations of aspects of one or more of the adjuvants identified above. For example, the following adjuvant compositions may be used in the invention: (1) a saponin and an oil-in-water emulsion [101]; (2) a saponin (e.g. QS21)+a non-toxic LPS derivative (e.g. 3dMPL) [102]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [103]; (5) combinations of 3dMPL with, for example, QS21 and/or oil-in-water emulsions [104]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 38.

The use of aluminium salt adjuvants is particularly preferred, and antigens are generally adsorbed to such salts. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Not all vesicles need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response in a patient that has already been primed against *N. meningitidis*. Subcutaneous and intranasal prime/boost regimes for OMVs are disclosed in ref. 105.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides OMV compositions and mixtures of the invention for use as a medicament. The medicament is preferably able to raise an immune response in a mammal (i.e. it is an immunogenic composition) and is more preferably a vaccine.

The invention also provides the use of OMV compositions and mixtures of the invention in the manufacture of a medicament for raising an immune response in a mammal.

These uses and methods are preferably for the prevention and/or treatment of a disease caused by *N. meningitidis* e.g. bacterial (or, more specifically, meningococcal) meningitis, or septicemia.

One way of checking efficacy of therapeutic treatment involves monitoring Neisserial infection after administration of the composition of the invention. One way of checking efficacy of prophylactic treatment involves monitoring immune responses against OMV antigens after administration of the composition. Immunogenicity of compositions of the invention can be determined by administering them to test subjects (e.g. children 12-16 months age, or animal models [106]) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined. The OMV-based RIVM vaccine was tested using a 3- or 4-dose primary schedule, with vaccination at 0. 2 & 8 or 0, 1, 2 & 8 months. MeNZB™ is administered as three doses at six week intervals.

As described above, the invention may involve administration of vesicles from more than one serosubtype of *N. meningitidis*, either separately or in admixture.

The invention may be used to elicit systemic and/or mucosal immunity.

In general, compositions of the invention are able to induce serum bactericidal antibody responses after being administered to a subject. These responses are conveniently measured in mice and are a standard indicator of vaccine efficacy [e.g. see end-note 14 of reference 166]. Serum bactericidal activity (SBA) measures bacterial killing mediated by complement, and can be assayed using human or baby rabbit complement. WHO standards require a vaccine to induce at least a 4-fold rise in SBA in more than 90% of recipients. MeNZB™ elicits a 4-fold rise in SBA 4-6 weeks after administration of the third dose.

By mixing OMVs for different serosubtypes, compositions of the invention may induce bactericidal antibody responses against more than one hypervirulent lineage of meningococcus. In particular, they can preferably induce bactericidal responses against two or three of the following three hypervirulent lineages: (i) cluster A4; (ii) ET5 complex; and (iii) lineage 3. They may additionally induce bactericidal antibody responses against one or more of hypervirulent lineages subgroup I, subgroup III, subgroup IV-1 or ET-37 complex, and against other lineages e.g. hyperinvasive lineages. This does not necessarily mean that the composition can induce bactericidal antibodies against each and every strain of meningococcus within these hypervirulent lineages e.g. rather, for any given group of four of more strains of meningococcus within a particular hypervirulent lineage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) e.g. the serum is able to kill at least 50% of test bacteria of a particular strain when diluted 1/1024, as described in reference 166.

Preferred compositions can induce bactericidal responses against the following strains of serogroup B meningococcus: (i) from cluster A4, strain 961-5945 (B:2b:P1.21,16) and/or strain G2136 (B:-); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (B:NT:-). More preferred compositions can induce bactericidal responses against strains 961-5945, 44/76 and 394/98.

Strains 961-5945 and G2136 are both *Neisseria* MLST reference strains [ids 638 & 1002 in ref. 107]. Strain MC58 is widely available (e.g. ATCC BAA-335) and was the strain sequenced in reference 108. Strain 44/76 has been widely used and characterised (e.g. ref. 109) and is one of the *Neisseria* MLST reference strains [id 237 in ref. 107; row 32 of Table 2 in ref. 19]. Strain 394/98 was originally isolated in New Zealand in 1998, and there have been several published studies using this strain (e.g. refs. 110 & 111). Strain BZ198 is another MLST reference strain [id 409 in ref. 107; row 41 of Table 2 in ref. 19].

Further Antigenic Components

As well as containing OMVs, compositions of the invention may include further non-vesicular antigens. For example, the composition may comprise one or more of the following further antigens:

a saccharide antigen from *N. meningitidis* serogroup A, C, W135 and/or Y, such as the oligosaccharide disclosed in ref. 112 from serogroup C or the oligosaccharides of ref. 113. The VA-MENINGOC-BC™ product contains serogroup C polysaccharide.

a saccharide antigen from *Streptococcus pneumoniae* [e.g. refs. 114-116; ch. 22 & 23 of ref. 123].

an antigen from hepatitis A virus, such as inactivated virus [e.g. 117,118; chapter 15 of ref. 123].

an antigen from hepatitis B virus, such as the surface and/or core antigens [e.g. 118,119; chapter 16 of ref. 123].

an antigen from hepatitis C virus [e.g. 120].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 121 & 122; chapter 21 of ref. 123].

a diphtheria antigen, such as a diphtheria toxoid [e.g. chapter 13 of ref. 123].

a tetanus antigen, such as a tetanus toxoid [e.g. chapter 27 of ref. 123].

a saccharide antigen from *Haemophilus influenzae* B [e.g. chapter 14 of ref. 123]

an antigen from *N. gonorrhoeae* [e.g. ref. 124].

an antigen from *Chlamydia pneumoniae* [e.g. 125-131].

an antigen from *Chlamydia trachomatis* [e.g. 132].

an antigen from *Porphyromonas gingivalis* [e.g. 133].

polio antigen(s) [e.g. 134, 135; chapter 24 of ref. 123] such as IPV.

rabies antigen(s) [e.g. 136] such as lyophilised inactivated virus [e.g. 137, RabAvert™].

measles, mumps and/or rubella antigens [e.g. chapters 19, 20 and 26 of ref. 123].

influenza antigen(s) [e.g. chapters 17 & 18 of ref. 123], such as the haemagglutinin and/or neuraminidase surface proteins.

an antigen from *Moraxella catarrhalis* [e.g. 138].

a protein antigen from *Streptococcus agalactiae* (group B streptococcus) [e.g. 139, 140].

an antigen from *Streptococcus pyogenes* (group A streptococcus) [e.g. 140, 141, 142].

Where a saccharide or carbohydrate antigen is used, it is preferably conjugated to a carrier in order to enhance immunogenicity. Conjugation of *H. influenzae* B, meningococcal and pneumococcal saccharide antigens is well known.

Toxic protein antigens may be detoxified where necessary (e.g. detoxification of *pertussis* toxin by chemical and/or genetic means [122]).

Where a diphtheria antigen is included in the composition it is preferred also to include tetanus antigen and *pertussis* antigens. Similarly, where a tetanus antigen is included it is preferred also to include diphtheria and *pertussis* antigens. Similarly, where a *pertussis* antigen is included it is preferred also to include diphtheria and tetanus antigens. DTP combinations are thus preferred.

Saccharide antigens are preferably in the form of conjugates. Preferred carrier proteins for conjugates are bacterial toxins or toxoids, such as diphtheria toxoid or tetanus toxoid. The CRM197 mutant of diphtheria toxin [143-145] is a particularly preferred carrier for, as is a diphtheria toxoid. Other suitable carrier proteins include the *N. meningitidis* outer membrane protein [146], synthetic peptides [147,148], heat shock proteins [149,150], *pertussis* proteins [151,152], cytokines [153], lymphokines [153], hormones [153], growth factors [153], artificial proteins comprising multiple human CD4$^+$ T cell epitopes from various pathogen-derived antigens [154], protein D from *H. influenzae* [155,156], pneumococcal surface protein PspA [157], pneumolysin [158], iron-uptake proteins [159], toxin A or B from *C. difficile* [160], etc.

Antigens in the composition will typically be present at a concentration of at least 1 μg/ml each. In general, the concentration of any given antigen will be sufficient to elicit an immune response against that antigen.

As an alternative to using protein antigens in the composition of the invention, nucleic acid encoding the antigen may be used. Protein components of the compositions of the invention may thus be replaced by nucleic acid (preferably DNA e.g. in the form of a plasmid) that encodes the protein.

Preferred compositions include meningococcal OMVs as described above, plus a conjugated capsular saccharide from one or more (i.e. 1, 2, 3 or 4) of meningococcal serogroups A, C, W135 and Y. Where the OMVs are from serogroup B then this approach allows the following serogroups to be covered: B+A; B+C; B+W135; B+Y; B+C+W135; B+C+Y; B+W135+Y; B+A+C+W135; B+A+C+Y; B+A+W135+Y; B+C+W135+Y; and B+A+C+W135+Y. Two preferred combinations use serogroup B OMVs plus conjugate antigens from either serogroups A+W135+Y or serogroups A+C+W135+Y. In general, it is possible to cover all five of serogroups A, B, C, W135 and Y by choosing OMVs for x serogroup(s) and conjugated saccharides for the remaining 5-x serogroups.

Specific meningococcal protein antigens (preferably from serogroup B) may also be added to supplement the OMV compositions. In particular, a protein antigen such as disclosed in refs. 30 & 161 to 169 may be added. A small number of defined antigens may be added (a mixture of 10 or fewer (e.g. 9, 8, 7, 6, 5, 4, 3, 2) purified antigens). Preferred additional immunogenic polypeptides for use with the invention are those disclosed in reference 169: (1) a 'NadA' protein; (2) a '741' protein; (3) a '936' protein; (4) a '953' protein; and (5) a '287' protein. Other possible supplementing meningococcal antigens include transferrin binding proteins (e.g. ThpA and TbpB) and/or Cu,Zn-superoxide dismutase [7]. Other possible supplementing meningococcal antigens include proteins comprising one of the following amino acid sequences: SEQ ID NO:650 from ref. 161; SEQ ID NO:878 from ref. 161; SEQ ID NO:884 from ref. 161; SEQ ID NO:4 from ref. 162; SEQ ID NO:598 from ref. 163; SEQ ID NO:818 from ref. 163; SEQ ID NO:864 from ref. 163; SEQ ID NO:866 from ref. 163; SEQ ID NO:1196 from ref. 163; SEQ ID NO:1272 from ref. 163; SEQ ID NO:1274 from ref. 163; SEQ ID NO:1640 from ref. 163; SEQ ID NO:1788 from ref. 163; SEQ ID NO:2288 from ref. 163; SEQ ID NO:2466 from ref. 163; SEQ ID NO:2554 from ref. 163; SEQ ID NO:2576 from ref. 163; SEQ ID NO:2606 from ref. 163; SEQ ID NO:2608 from ref. 163; SEQ ID NO:2616 from ref. 163; SEQ ID NO:2668 from ref. 163; SEQ ID NO:2780 from ref. 163; SEQ ID NO:2932 from ref. 163; SEQ ID NO:2958 from ref. 163; SEQ ID NO:2970 from ref. 163; SEQ ID NO:2988 from ref. 163, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6) of these polypeptides may be included. The meningococcal antigens transferrin binding protein and/or Hsf protein may also be added [170].

Supplementation of the OMVs by defined meningococcal antigens in this way is particularly useful where the OMVs are from a serosubtype P1.7b,4 meningococcus or a serosubtype P1.7,16 meningococcus. Supplementation of a mixture of OMVs from both these serosubtypes is preferred.

Specific Serosubtypes

The invention provides a composition comprising OMVs prepared from a meningococcus having one of the following subtypes: P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14

The meningococcus is preferably in serogroup B.

These OMVs are suitable for use with the invention, as described above.

OMV Administration Regime

The invention provides a method for administering a meningococcal OMV vaccine to a patient, wherein a first dose is given at time zero, a second and a third dose are given over the next two months, and a fourth dose is given between 11 and 13 months after time zero.

The invention also provides a method for administering meningococcal OMV vaccines to a patient, wherein a first dose is given at time zero, a second and a third dose are given over the next two months, and a fourth dose is given between 11 and 13 months after time zero, and wherein (a) the first, second and third doses comprise OMVs with the same serosubtype as each other, and (b) the fourth dose comprises OMVs with a different serosubtype from the first three doses. The fourth dose may contain OMVs only with a different serosubtype from the first three doses, or it may contain two types of OMV, one with a different serosubtype from the first three doses and one with the same subtype.

The first, second and third doses are preferably given at intervals of between 6 and 8 weeks. The fourth dose is preferably given about 1 year after time zero.

The patient preferably receives the same quantity of vaccine at each of the four doses.

The OMVs are preferably serosubtype P1.7b,4 and/or P1.7,16.

The invention also provides a method for administering a meningococcal vaccine to a patient, wherein: (a) the vaccine comprises meningococcal OMVs having a first serosubtype; (b) the patient has previously received a different OMV vaccine having a second serosubtype, with the first dose of the different OMV vaccine was given more than 11 months before this method.

The invention also the use of meningococcal OMVs having a first serosubtype in the manufacture of a medicament for immunising against meningococcal meningitis, wherein the medicament is for administration to a patient that has been pre-immunised with OMVs having a second serosubtype. OMV administration may also follow immunisation with a meningococcal conjugate vaccine. Thus the invention provides the use of meningococcal OMVs from a first meningococcal serogroup in the manufacture of a medicament for immunising against at least meningococcal meningitis, wherein the medicament is for administration to a patient that has been pre-immunised with a conjugated capsular saccharide from a second meningococcal serosubtype. Similarly, it provides a method for administering a meningococcal vaccine to a patient, wherein: (a) the vaccine comprises meningococcal OMVs having a first serogroup; (b) the patient has previously received a conjugated capsular saccharide from a second meningococcal serogroup.

The pre-immunisation may have taken place more than 6 months before the OMVs are administered (e.g. more than 11 months). Thus, for instance, a patient may receive conjugated saccharides at time zero, and then OMVs 11 months later.

The pre-inmunisation with a meningococcal saccharide is preferably with at least serogroup C, but may be with more than one serogroup e.g. with both A+C, with A+C+Y, with A+C+W135+Y, etc.

The first serogroup is preferably serogroup B.

The OMVs may be administered at the same time as meningococcal conjugates i.e. the patient is receiving a further dose of meningococcal conjugate at the same time as receiving the OMVs.

The patient may or may not have been pre-immunised with OMVs from the first serogroup.

The patient may have been pre-immunised with a *H. influenzae* type b capsular saccharide conjugate.

The patient may have been pre-immunised with a diphtheria toxoid and a tetanus toxoid.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

OMV Dosage—Single Strain

Dosing studies for the MeNZB™ product were performed on healthy adults. Adults received three doses of either 25 µg or 50 µg of OMV, given at 6 week intervals through a 25 mm 23-gauge needle. A four-fold rise in SBA titre against the vaccine strain, measured 4 to 6 weeks after the third vaccination, was seen in 100% of patients receiving the 25 µg dose but, surprisingly, was seen in only 87% of patients receiving the higher dose. The proportion of responders was also higher at the lower dosage after the second dose (87% vs. 78%). The lower dose was therefore selected for further use, thereby permitting stocks of vaccine to provide for immunisation of twice as many patients.

OMV Dosage—Multiple Combined Strains

OMVs prepared from Norwegian strain H44/76 have previously been described and administered to human patients in phase I, II and III clinical trials. They form the basis of the MenBvac™ product. Similarly, OMVs prepared from New Zealand strain HZ98/254 form the basis of the MeNZB™ product. Their safety and efficacy have been confirmed.

Both MeNZB™ and MenBvac™ include OMVs at a concentration of 50 µg/ml (measured as amount of protein) in a 0.5 ml dose. When testing a combination of the two OMVs in humans then, in order to maintain efficacy against the two different serosubtypes, the most direct comparison would be to keep the concentration of each OMV at 50 µg/ml. In contrast, the inventors chose to keep the total OMV dose the same as in the two monovalent products (50 µg/ml) and instead to halve the amount of each OMV i.e. to use 25 µg/ml of each serosubtype.

The combined vaccine is administered to patients who have previously received either MeNZB™ or MenBvac™. The combination is given 1 year after the initial dose of the monovalent OMVs.

It will be understood that the invention has been described by way of example only and modifications may be made whilst remaining within the scope and spirit of the invention.

REFERENCES

The Contents of Which are Hereby Incorporated by Reference

[1] Bjune et al. (1991) *Lancet* 338(8775):1093-1096.
[2] de Kleijn et al. (2001) *Vaccine* 20:352-358.
[3] U.S. Pat. Nos. 5,597,572 & 5,747,653; see also European patent 0301992.
[4] European patent 0449958 (granted from WO90/06696).
[5] U.S. Pat. No. 5,705,161; see also WO94/08021.
[6] WO01/91788.
[7] WO00/25811.
[8] WO01/52885.
[9] WO98/56901.
[10] Sacchi et al. (1998) *Rev Inst Med Trop Sao Paulo* 40:65-70.
[11] WO03/105890.
[12] WO02/09643.
[13] Katial et al. (2002) *Infect. Immun.* 70:702-707.
[14] U.S. Pat. No. 6,180,111.
[15] WO01/34642.
[16] European patent 0011243.
[17] Fredriksen et al. (1991) *NIPH Ann.* 14(2):67-80.
[18] PCT/IB2004/002475
[19] Maiden et al. (1998) *PNAS USA* 95:3140-3145.
[20] WO99/10497.
[21] Steeghs et al. (2001) *The EMBO Journal* 20:6937-6945.
[22] WO02/07763.
[23] European patent 0624376.
[24] van der Ley et al. (1995) *Vaccine* 13:401-7.
[25] WO01/09350.
[26] WO02/09746.
[27] WO02/062378.
[28] WO2004/014417.
[29] WO2004/019977.
[30] WO2004/048404.
[31] Masignani et al. (2003) *J Exp Med* 197:789-799.
[32] Gennaro (2000) *Remington: The Science and Practice of Pharmacy.* 20th edition, ISBN: 0683306472.
[33] RIVM report 124001 004.
[34] RIVM report 000012 003.
[35] WO03/009869.
[36] Almeida & Alpar (1996) *J. Drug Targeting* 3:455-467.
[37] Agarwal & Mishra (1999) *Indian J Exp Biol* 37:6-16.
[38] Vaccine Design . . . (1995) eds. Powell & Newman. ISBN: 030644867X. Plenum.
[39] WO00/23105.
[40] WO90/14837.
[41] U.S. Pat. No. 5,057,540.
[42] WO96/33739.
[43] EP-A-0109942.
[44] WO96/11711.
[45] WO00/07621.
[46] Barr et al. (1998) *Advanced Drug Delivery Reviews* 32:247-271.
[47] Sjolanderet et al. (1998) *Advanced Drug Delivery Reviews* 32:321-338.
[48] Niikura et al. (2002) *Virology* 293:273-280.
[49] Lenz et al. (2001) *J Immunol* 166:5346-5355.
[50] Pinto et al. (2003) *J Infect Dis* 188:327-338.
[51] Gerber et al. (2001) *Virol* 75:4752-4760.
[52] WO03/024480
[53] WO03/024481
[54] Gluck et al. (2002) *Vaccine* 20:B10-B16.
[55] EP-A-0689454.

[56] Johnson et al. (1999) *Bioorg Med Chem Lett* 9:2273-2278.
[57] Evans et al. (2003) *Expert Rev Vaccines* 2:219-229.
[58] Meraldi et al. (2003) *Vaccine* 21:2485-2491.
[59] Pajak et al. (2003) *Vaccine* 21:836-842.
[60] Kandimalla et al. (2003) *Nucleic Acids Research* 31:2393-2400.
[61] WO02/26757.
[62] WO99/62923.
[63] Krieg (2003) *Nature Medicine* 9:831-835.
[64] McCluskie et al. (2002) *FEMS Immunology and Medical Microbiology* 32:179-185.
[65] WO98/40100.
[66] U.S. Pat. No. 6,207,646.
[67] U.S. Pat. No. 6,239,116.
[68] U.S. Pat. No. 6,429,199.
[69] Kandimalla et al. (2003) *Biochemical Society Transactions* 31 (part 3):654-658.
[70] Blackwell et al. (2003) *J Immunol* 170:4061-4068.
[71] Krieg (2002) *Trends Immunol* 23:64-65.
[72] WO01/95935.
[73] Kandimalla et al. (2003) *BBRC* 306:948-953.
[74] Bhagat et al. (2003) *BBRC* 300:853-861.
[75] WO03/035836.
[76] WO95/17211.
[77] WO98/42375.
[78] Beignon et al. (2002) *Infect Immun* 70:3012-3019.
[79] Pizza et al. (2001) *Vaccine* 19:2534-2541.
[80] Pizza et al. (2000) *Int J Med Microbiol* 290:455-461.
[81] Scharton-Kersten et al. (2000) *Infect Immun* 68:5306-5313.
[82] Ryan et al. (1999) *Infect Immun* 67:6270-6280.
[83] Partidos et al. (1999) *Immunol Lett* 67:209-216.
[84] Peppoloni et al. (2003) *Expert Rev Vaccines* 2:285-293.
[85] Pine et al. (2002) *J Control Release* 85:263-270.
[86] Domenighini et al. (1995) *Mol Microbiol* 15:1165-1167.
[87] WO99/40936.
[88] WO99/44636.
[89] Singh et al] (2001) *J Cont Release* 70:267-276.
[90] WO99/27960.
[91] U.S. Pat. No. 6,090,406
[92] U.S. Pat. No. 5,916,588
[93] EP-A-0626169.
[94] WO99/52549.
[95] WO01/21207.
[96] WO01/21152.
[97] Andrianov et al. (1998) *Biomaterials* 19:109-115.
[98] Payne et al. (1998) *Adv Drug Delivery Review* 31:185-196.
[99] Stanley (2002) *Clin Exp Dermatol* 27:571-577.
[100] Jones (2003) *Curr Opin Investig Drugs* 4:214-218.
[101] WO99/11241.
[102] WO94/00153.
[103] WO98/57659.
[104] European patent applications 0835318, 0735898 and 0761231.
[105] Bakke et al. (2001) *Infect. Immun.* 69:5010-5015.
[106] WO01/30390.
[107] http://*neisseria*.org/nm/typing/mlst/
[108] Tettelin et al. (2000) *Science* 287:1809-1815.
[109] Pettersson et al. (1994) *Microb Pathog* 17(6):395-408.
[110] Welsch et al. (2002) Thirteenth International Pathogenic *Neisseria* Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[111] Santos et al. (2002) Thirteenth International Pathogenic *Neisseria* Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[112] Costantino et al. (1992) *Vaccine* 10:691-698.
[113] WO03/007985.
[114] Watson (2000) *Pediatr Infect Dis J* 19:331-332.
[115] Rubin (2000) *Pediatr Clin North Am* 47:269-285, v.
[116] Jedrzejas (2001) *Microbiol Mol Biol Rev* 65:187-207.
[117] Bell (2000) *Pediatr Infect Dis J* 19:1187-1188.
[118] Iwarson (1995) *APMIS* 103:321-326.
[119] Gerlich et al. (1990) *Vaccine* 8 Suppl:S63-68 & 79-80.
[120] Hsu et al. (1999) *Clin Liver Dis* 3:901-915.
[121] Gustafsson et al. (1996) *N. Engl. J. Med.* 334:349-355.
[122] Rappuoli et al. (1991) *TIBTECH* 9:232-238.
[123] *Vaccines* (2004) eds. Plotkin & Orenstein. ISBN 0-7216-9688-0.
[124] WO02/079243.
[125] WO02/02606.
[126] Kalman et al. (1999) *Nature Genetics* 21:385-389.
[127] Read et al. (2000) *Nucleic Acids Res* 28:1397-406.
[128] Shirai et al. (2000) *J. Infect. Dis.* 181(Suppl 3):S524-S527.
[129] WO99/27105.
[130] WO00/27994.
[131] WO00/37494.
[132] WO99/28475.
[133] Ross et al. (2001) *Vaccine* 19:4135-4142.
[134] Sutter et al. (2000) *Pediatr Clin North Am* 47:287-308.
[135] Zimmerman & Spann (1999) *Am Fam Physician* 59:113-118, 125-126.
[136] Dreesen (1997) *Vaccine* 15 Suppl:S2-6.
[137] *MMWR Morb Mortal Wkly Rep* Jan. 16, 1998; 47(1):12, 19.
[138] McMichael (2000) *Vaccine* 19 Suppl 1:S101-107.
[139] Schuchat (1999) *Lancet* 353(9146):51-6.
[140] WO02/34771.
[141] Dale (1999) *Infect Dis Clin North Am* 13:227-43, viii.
[142] Ferretti et al. (2001) *PNAS USA* 98: 4658-4663.
[143] Anonymous (January 2002) *Research Disclosure*, 453077.
[144] Anderson (1983) *Infect Immun* 39(1):233-238.
[145] Anderson et al. (1985) *J Clin Invest* 76(1):52-59.
[146] EP-A-0372501.
[147] EP-A-0378881.
[148] EP-A-0427347.
[149] WO93/17712
[150] WO94/03208.
[151] WO98/58668.
[152] EP-A-0471177.
[153] WO91/01146
[154] Falugi et al. (2001) *Eur J Immunol* 31:3816-3824.
[155] EP-A-0594610.
[156] WO00/56360.
[157] WO02/091998.
[158] Kuo et al. (1995) *Infect Immun* 63:2706-13.
[159] WO01/72337
[160] WO00/61761.
[161] WO99/24578.
[162] WO99/36544.
[163] WO99/57280.
[164] WO00/22430.
[165] WO96/29412.
[166] Pizza et al. (2000) *Science* 287:1816-1820.
[167] WO01/64920.

[168] WO03/020756.
[169] WO2004/032958.
[170] WO2004/014419.

The invention claimed is:

1. A composition comprising an admixture of outer membrane vesicles (OMVs) from a first meningococcus strain and a second meningococcus strain, wherein the first meningococcus strain is serosubtype P1.7-2,4, the concentration of OMVs from the first meningococcus strain is about 25 µg protein/mL, the concentration of OMVs from the second meningococcus strain is about 25 µg protein/mL, and the volume of the composition is 0.5 mL.

2. The composition of claim 1, further comprising a conjugated capsular saccharide from one or more of meningococcal serogroups A, C, W135 and Y.

3. The composition of claim 1, wherein the first or the second meningococcus strain has a knockout of one or more enzymes involved in LPS biosynthesis.

4. The composition of claim 1, wherein the first or the second meningococcus strain over-expresses an immunogen selected from the group consisting of NspA, protein 287, protein 741, TbpA, TbpB, and superoxide dismutase.

5. The composition of claim 1, comprising less than 0.4 µg of deoxycholate for every µg of protein.

6. The composition of claim 1, comprising less than 0.12 µg of meningococcal LPS for every µg of protein.

7. The composition of claim 1, comprising an aluminum hydroxide adjuvant.

8. The composition of claim 1, wherein the composition includes an aluminum hydroxide adjuvant and a histidine buffer.

9. The composition of claim 1, further comprising a conjugated capsular saccharide from two or more of meningococcal serogroups A, C, W135 and Y.

10. A kit comprising separate containers of outer membrane vesicles (OMVs) from a first meningococcus strain and a second meningococcus strain, wherein the first meningococcus strain is serosubtype P1.7-2,4 and after resuspension of the OMVs from both containers in 0.5 mL, the concentration of OMVs from the first meningococcus strain is about 25 µg protein/mL and the concentration of OMVs from the second meningococcus strain is about 25 µg protein/mL.

11. The kit of claim 10, further comprising a conjugated capsular saccharide from one or more of meningococcal serogroups A, C, W135 and Y.

12. A method for administering a meningococcal OMV vaccine comprising the composition of claim 1 to a patient, wherein a first dose is given at time zero, a second and a third dose are given over the next two months, and a fourth dose is given between 11 and 13 months after time zero.

* * * * *